(12) United States Patent
Watzke et al.

(10) Patent No.: US 11,701,207 B2
(45) Date of Patent: Jul. 18, 2023

(54) METHOD OF PRODUCING A DENTAL PROSTHESIS

(71) Applicant: Ivoclar Vivadent AG, Schaan (LI)

(72) Inventors: Ronny Watzke, Feldkirch (AT); Christian Frei, Naturns (IT)

(73) Assignee: Ivoclar Vivadent AG, Schaan (LI)

( * ) Notice: Subject to any disclaimer, the term of this patent is extended or adjusted under 35 U.S.C. 154(b) by 567 days.

(21) Appl. No.: 16/823,891

(22) Filed: Mar. 19, 2020

(65) Prior Publication Data
US 2020/0214812 A1    Jul. 9, 2020

Related U.S. Application Data

(62) Division of application No. 15/554,481, filed as application No. PCT/EP2016/054266 on Mar. 1, 2016, now Pat. No. 10,646,311.

(30) Foreign Application Priority Data

Mar. 4, 2015 (EP) ..................................... 15157544

(51) Int. Cl.
*A61C 13/08* (2006.01)
*A61C 13/00* (2006.01)
(Continued)

(52) U.S. Cl.
CPC ............ *A61C 13/082* (2013.01); *A61C 13/00* (2013.01); *A61C 13/0004* (2013.01); *A61C 13/0022* (2013.01); *A61C 13/09* (2013.01); *A61C 13/0006* (2013.01); *A61C 13/01* (2013.01); *G16H 20/40* (2018.01)

(58) Field of Classification Search
CPC ... A61C 13/082; A61C 13/00; A61C 13/0004; A61C 13/0022; A61C 13/09; A61C 13/0006; A61C 13/01; G16H 20/40
See application file for complete search history.

(56) References Cited

U.S. PATENT DOCUMENTS

| 4,403,961 | A |   | 9/1983 | Gurney |
|---|---|---|---|---|
| 5,672,305 | A | * | 9/1997 | Kogure ................. A61C 13/20 264/102 |

(Continued)

FOREIGN PATENT DOCUMENTS

| CN | 2490991 Y | 5/2002 |
|---|---|---|
| CN | 103654981 A | 3/2014 |

(Continued)

*Primary Examiner* — Rick K Chang
(74) *Attorney, Agent, or Firm* — Ann M. Knab; Thad McMurray (57) ABSTRACT

The invention relates to a method of producing a dental prosthesis from a one-piece or multi-piece prosthesis blank which is constructed from a gum-colored material and a tooth-colored material (32), in particular in each case on a plastic base. It is characterized by being connected to each other at connecting surfaces, having an interface between the gum-colored and tooth-colored materials. This interface, when viewed along the connecting surfaces has an undulating shape and viewed in the vestibular direction has a radial shape. In order to finish the dental prosthesis, a CAD/CAM device determines the exact course of a gingival line, based on patient-specific data, and produces the prosthesis.

15 Claims, 7 Drawing Sheets

(51) Int. Cl.
  *A61C 13/09*   (2006.01)
  *A61C 13/01*   (2006.01)
  *G16H 20/40*   (2018.01)

(56) References Cited

U.S. PATENT DOCUMENTS

| | | | |
|---|---|---|---|
| 5,823,778 A * | 10/1998 | Schmitt | A61C 13/0004 433/214 |
| 8,195,320 B2 | 6/2012 | Garcia-Aparicio | |
| 8,932,058 B2 | 1/2015 | Fisker et al. | |
| 9,192,456 B2 * | 11/2015 | Howe | A61C 13/081 |
| 10,251,733 B2 * | 4/2019 | Grobbee | A61C 13/09 |
| 10,828,135 B2 * | 11/2020 | Thompson | A61C 13/10 |
| 2012/0258430 A1 * | 10/2012 | Ruppert | A61C 13/0004 433/199.1 |
| 2013/0101962 A1 * | 4/2013 | Howe | A61C 13/0006 264/17 |
| 2014/0308624 A1 * | 10/2014 | Lee | A61C 13/0004 433/214 |
| 2014/0317930 A1 | 10/2014 | Klingenburg et al. | |

FOREIGN PATENT DOCUMENTS

| | | |
|---|---|---|
| EP | 0850601 A2 | 7/1998 |
| FR | 2992163 A3 | 12/2013 |
| JP | H09238957 A | 9/1997 |
| WO | 2010057584 A1 | 5/2010 |
| WO | 2013117540 A1 | 8/2013 |

\* cited by examiner

METHOD OF PRODUCING A DENTAL PROSTHESIS

CROSS-REFERENCE TO RELATED APPLICATIONS

This application claims priority to and is a Divisional Application of U.S. application Ser. No. 15/554,481, filed on Aug. 30, 2017, which is the National Stage application of International patent application PCT/EP2016/054266 filed on Mar. 1, 2016, which claims priority to European patent application No. 15157544.6 filed on Mar. 4, 2015, all the disclosures of which are incorporated herein by reference in their entirety.

TECHNICAL FIELD

The invention relates to a method of producing a dental prosthesis.

BACKGROUND

It has been known for long to construct prostheses, and also teeth, from several layers.

It is referred to the solutions known from WO 90/13268 A1 and WO 91/07141 A1 for examples thereof.

Based on these relatively old solutions, multi-layered plastic elements produced with the aid of CAD/CAM technology have been suggested recently which serve to produce teeth and prostheses in order to provide for teeth and the prosthesis base to provide for a finished prosthesis. Due to the different requirements to the various materials, namely the gum-colored prosthesis base material on the one hand and the tooth-colored tooth material on the other hand, this suggestion has not yet become established, even although it has become known otherwise to produce teeth and a prosthesis base from PMMA.

Furthermore, rapid prototyping methods have been suggested recently, aiming to provide teeth and prosthesis bases from a plastic material—or possibly from other materials, too. This development has not yet experienced proper progress either up to now.

On the other hand, with respect to the increasing life expectancy there is an increasing demand for full and partial prostheses, and for reasons of simplicity the term prostheses comprises full as well as partial prostheses herein. This increasing demand is coupled with an also increasing pressure on costs, already due to the considerably increasing demand which is to be expected.

SUMMARY

Thus, the invention is based on the task of providing a prosthesis constructed from a gum-colored material and a tooth-colored material, and a method of producing a dental prosthesis constructed from a gum-colored material and a tooth-colored material, wherein said prosthesis can be produced cost-effectively and also offers considerably improved acceptance and is also optimized with regard to storage possibilities This task is inventively solved by claim 1. Advantageous further developments may be taken from the subclaims.

It is provided with dental prostheses which are produced to be in one piece or part in one embodiment, and in two pieces or parts in another embodiment, to connect the two materials with one another in a special way. As viewed along the extension of the gingival arch of the prosthesis, the shape is wave-shaped, wherein the term wave-shaped also includes an asymmetrical wave herein, that is to say a shape in which—similar to a catenary—small and narrow arches alternate with deep and wide arches.

A particular advantage is due to the fact that the wave shape of the prosthesis extends radially as viewed from a central point thereof. Thus, every wave trough and every wave crest extends on the same height, or in a modified embodiment on a straight line which may deviate from the horizontal by a few degrees, for instance by 10°, to the top or to the bottom.

It is particularly favorable that the teeth of the gingival arch remain connected to one another, but still appear to be individual teeth due to the deep grooves between the teeth as viewed from the vestibular direction. The reason for this is among others that particularly in the anterior tooth region light incident from the side casts shadows such that the interdental spaces are shadowed by at least one neighboring tooth, and in this respect the inventive multi-tooth arch may not be differentiated from individual teeth.

The gum-colored material and the tooth-colored material are intensively connected to one another to produce the inventive two-colored blank—either by a one-piece production, or by bonding or polymerizing. The one-piece and inseparable production can be achieved, for instance, in that the materials are pressed onto one another in a state which is still soft—or even liquid—at the interface, such that they penetrate into one another—when viewed through a microscope. However, with this type of production, too, the transition area is in the submillimeter range, for instance, as thick as less than 100 µm.

Even in layer polymerization there is such a transition area having the same size, and in bonding processes the adhesive joint can have a low thickness of, for instance, between 40 and 200 µm.

Preferably, the blank of gum-colored material is at least partially shaped like a circular arc. The realization by means of a disc has proven to be particularly favorable, wherein, for instance, in a circular disc having a diameter of 98.5 mm two prosthesis bases may easily be accommodated. In the blank state, the tooth-colored material of the blank has a size which is larger than a human dental arch, that is to say preferably larger than 8 cm.

In the same manner the material input for the production of the tooth-colored blank may be optimized. In case of full prosthetic dentistry, for instance, a circular disc having the same diameter can receive a plurality of dental arches. It is possible, for instance, to realize two relatively large dental arches opposite from one another in a way known per se. In the case of lower jaw prostheses the arches can be realized substantially as parabolas, and in the case of upper jaw prostheses in the form of ellipses.

It is favorable that the wave crests of the tooth-colored material are provided at tooth positions and the wave troughs at interdental space positions. In this way, after the finishing process, for instance by a common milling process, the appearance will resemble the natural gingival margin.

In this way, when the material is utilized ideally, for instance up to six dental arches may be milled from a tooth-colored blank disc, wherein it is to be understood that in the realization of partial prostheses this number can even be increased considerably. It is also possible to attach a dental arch blank to the upper side of a gum-colored prosthesis blank, and a further one to the lower side thereof—offset by 180°—such that upper jaw and lower jaw prostheses may be produced in one go.

In a further advantageous embodiment it is provided to integrate a reinforcement into the gum-colored prosthesis tooth carrier. It can, for instance, consist of metal or of any other suitable material, whose strength is larger than the strength of the gum-colored material. The reinforcement may either be integrated in advance, that is to say, for instance, in the gum-colored blank, or may be inserted, in particular, slid in, retrospectively by forming a pocket.

It is provided to connect the tooth-colored blank and the gum-colored blank with one another intensively in the preferred embodiment—be it by polymerizing or by bonding—and to carry out the required milling operation in this state. This has the advantage that the milling operations can take place considerably faster. Clamping is only necessary in the area of the gum-colored blank disc. Due to the intensive connection between the tooth-colored and the gum-colored blank and due to the positive-locking fit between them by means of the combined wave shape and radial shape the strength of the connection is also surprisingly sufficient for the milling operation and the forces applied thereat.

At the same time, this automatically tests the ability of the connection to cope with strain in view of the shear forces during mastication which will be applied later.

Here, the dental arch shape of the tooth-colored mass is particularly favorable which is considerably superior to an alternative solution having individual teeth in view of the strength of the connection.

According to the invention it is particularly favorable that the prosthesis—after having fixed the gum-colored and the tooth-colored material to one another—may be automatically finished by milling, in particular in a CAD/CAM unit, involving the control device. The control device makes it possible to determine the exact position of the vestibular border line of the interface automatically and/or in a user-controlled way.

In an advantageous embodiment of the invention it is provided that the gum-colored prosthesis blank is provided with one to four substantially semicircular wave arches for receiving the tooth-colored material. Each one of these wave arches has a radial character at the same time.

With a sophisticated arrangement, it is possible to produce at least two prostheses, in particular also of different sizes, from one disc of gum-colored material.

In a further embodiment it is provided that the interface—as viewed in the vestibular direction—has a further, in particular less strongly distinct wave line along its course.

Preferably, the exact course of the wave shape is adapted to the gingival line of the gingival margin of a human mouth. This holds particularly true for the anterior tooth region, while in the molar region more strongly pronounced wave crests and wave troughs are even possible in order to further improve the positive-locking fit of the connection.

In this respect, the inventive wave crests and wave troughs have a dual function:

On the one hand, by means of the positive-locking fit between the dental arch and the prosthesis base the strength is improved considerably and in this respect bonding is supported which can be carried out by way of this example instead of by a polymerization process.

On the other hand the red/white transition can be represented easily in this way, wherein it is to be understood that, in the finished prosthesis, every tooth-colored wave crest follows the exposed edge of the tooth at its tooth neck with respect to the gingiva formed by the gum-colored material.

A CAD/CAM device finishes the dental prosthesis, according to the invention, by determining the exact course of the gingival line, that is to say the vestibular border line of the interface as viewed from the occlusal direction, based on patient-specific data, and produces the prosthesis based thereon. In this way, the size of the prosthesis is determined in a patient-specific manner and different tooth arch shapes can also be accounted for, that is to say, for instance, slightly rounder or slightly more triangle-shaped shapes.

Providing the necessary patient data is carried out as follows:

Either, an intraoral scan is initially carried out in a way known per se, or an impression is taken and then a 3D scan thereof also in a way known per se.

Anatomically relevant points are marked and serve as reference points. The software of the CAD/CAM device is supplied with the data obtained in this way, and it automatically produces a suggestion for a prosthesis, a so-called virtual prosthesis, together with its control device. However, this prosthesis may be changed by the user, that is to say, for instance, by the dental technician, at the CAD/CAM device.

For instance, the course of the gingival line—as viewed from the occlusal direction—may be adapted easily based on aesthetic aspects.

Here, the control device also takes into account the dimensions and the geometry of the teeth, compared to the tooth arch blank and its dimensions. When it becomes apparent that the desired tooth arch would not fit into the blank, the software emits a corresponding alarm signal.

The same holds true for the prosthesis base blank which may also be referred to as gingival blank. When the size of the prosthesis base is larger than that of the intended blank at one position, an alarm signal is also emitted indicating that the blank next in size is to be used.

If the desired shape has been determined virtually, the obtained data is released for further machining. In the case of a subtractive production of the prosthesis, it is fed to a milling machine of the CAD/CAM device into which a bicolored inventive blank with a wave-shaped/radial interface is or will be clamped.

In the case of generative production, the data is fed to a rapid prototyping device in which the shape of the tooth arch blank and the prosthesis base blank is stored virtually with the inventive radial/wave-shaped interface. Based on the obtained patient-specific data and the design function of the CAD/CAM device the vestibular border line of the interface is constructed, and then the prosthesis is produced based thereon.

In any way, it is crucial that the tooth arch blank has an exact negative shape of the surface of the prosthesis base blank at the interface to the prosthesis base blank such that the two wave lines which extend radially fit to one another exactly and may be easily connected to one another intensively.

As a matter of fact, it is possible to produce, for instance, even five individual parts and then to suitably join or combine them in accordance with the requirements in order to provide the blank disc to the customer.

Then, the customer practically performs a milling operation from one solid piece of material, that is to say the tooth material and the gingival material at the same time.

In a modified embodiment, it is provided to premodulate one of the materials, for instance the prosthesis base, in view of the interface towards the tooth arch. In this embodiment, this radial wave shape is used as a base for casting without further ado, and then the tooth arch is cast onto it using a corresponding mold and then fully polymerized.

In this solution, too, an exactly predefined wave line having the desired gingival margin and a radial orientation with wave crests and wave troughs which become broader in the vestibular direction is produced.

By means of the control device the individual tooth shape, and also the rotation and the angulation of the teeth, and also the shape of the prosthesis base, may be determined based on the obtained patient data such that different designs of full prostheses may be produced.

The radial shape also ensures that, when the width increases—as viewed from the vestibular direction—the height of the teeth and wave crests increases at the same time. This corresponds to the anatomic conditions, as typically, when the tooth width increases, the dimensions of the teeth become larger in all three spatial directions such that a tooth which is positioned more to the rear (as viewed in the lingual/vestibular direction) is also broader (as viewed in the mesial/distal direction) and higher (as viewed in the occlusal-incisal/cervical direction) at the same time.

When the prosthesis base is present as a blank in the shape of a disc, it is preferred to insert semicircular wave arches into it. They serve to receive the tooth arches, wherein it is to be understood that the tooth arches have wave arches which match the wave arches of the gum-colored disc.

Surprisingly, it is possible in this way to provide aesthetically particularly well-made prostheses even with teeth of very different sizes, wherein it is also possible, for instance with partial prostheses, to configure a small tooth arch from a tooth-colored blank on the one hand, and afterwards or simultaneously, for instance, a large tooth arch at another position.

Then, in this way, the large tooth arch is attached to a gum-colored prosthesis base and the other tooth arch to another, also gum-colored prosthesis base, and the gum-colored material and the tooth-colored material are joined to one another at the boundary layer.

The materials can be connected both by bonding and by polymerizing onto one another, and due to the wave shape a positive-locking fit is effected additionally which counteracts masticatory forces which act in particular laterally.

Among the masticatory forces, the shear forces are particularly relevant which may amount to more than 1000 N as is well known (see, for instance, the dissertation "Entwicklung and Anwendung einer Methode zur Kaukraftmessung", Tobias Fink, Charité Berlin 2007).

In this connection, it is particularly favorable and increases the durability of the prosthesis to a surprising extent, that the positive-locking fit of the parts of the prosthesis stands the occurring alternating loads more easily.

In a modified embodiment, the teeth of the inventive prosthesis are connected to one another via bridges made of tooth-colored material which form the dental arch. In this way, compared to individual teeth, the lateral support against shear forces is improved by one order of magnitude.

By the way, this also holds true—albeit to a slightly smaller extent—for partial prostheses which are subsumed under the term prostheses according to the invention.

While individually produced and pre-fabricated teeth are typically received in tooth cavities in a prosthesis base which is produced according to prior art and are subjected to considerable shear stress due to the leverage effect of the masticatory forces during mastication, said shear forces also heavily straining the adhesive surface, it is provided inventively to absorb these shear forces over at least two wave crests and wave troughs positively. The dreaded leverage effect of the individual tooth with the leverage ratio of approximately 2:1 is eliminated as the dental arch provided in this way which comprises at least two adjacent teeth in case of partial prostheses has a considerably larger width than height such that the leverage effect of 2:1 is reduced to, for instance, 0.5:1.

It is to be understood that in case of complete dental arches which are required in case of full prostheses the respective leverage effect is reduced, for instance, to values of between 0.06:1 and 0.1:1, in correspondence with the height/width ratio of the tooth-colored material of the inventive prosthesis provided for each patient specifically.

In a modified embodiment, it is provided that the wave shape simulates the gingival margin as an interface between the materials. Of course, it is different from patient to patient, and it is particularly favorable in this respect that, with regard to the radial shape as viewed in the vestibular direction, the size, that is to say the width and the depth of the wave crests and wave troughs on the outside, that is to say on the vestibular side of the dental arch, may be adapted to the requirements.

For this purpose, the inventive control device for producing the inventive prosthesis easily determines the radial position of the dental arch—that is the position as viewed in the vestibular/palatal or lingual direction—and produces the desired dental arch determined by CAD, for instance, in a subtractive method together with the prosthesis base. For instance, this can be effected in a milling machine of the CAD/CAM device, as has been mentioned before.

The gum-colored and tooth-colored materials are connected with one another intensively, be it by adhesive bonding, be it by polymerizing or even by producing them from one piece of material.

In case of a two-piece production it is favorable that both materials can be connected to one another at any point in time and also in any selection fitting one another.

Then, semicircular wave arch receptions ensure that the full circle of the disc is utilized ideally. This applies to full prostheses, while smaller arch segments than semicircular arch segments, that is to say, for instance, 60° segments or similar, can also be taken into account for partial prostheses such that a larger number of partial prostheses may be produced cost-effectively and quickly from one single gum-colored disc.

In case of a full prosthesis, it is also possible to ensure that the wave shape—as viewed along the gingival arch—does not extend exactly horizontally but to lower it slightly in correspondence with the natural course of the teeth in the incisal area, for instance, by 1 mm, and accordingly to raise it in the molar area to take account for the Curve of Spee and the Curve of Wilson.

BRIEF DESCRIPTION OF THE DRAWINGS

Further advantages, details and features may be taken from the following description of several exemplary embodiments of the invention in conjunction with the drawings, in which.

DETAILED DESCRIPTION

Figure 1:
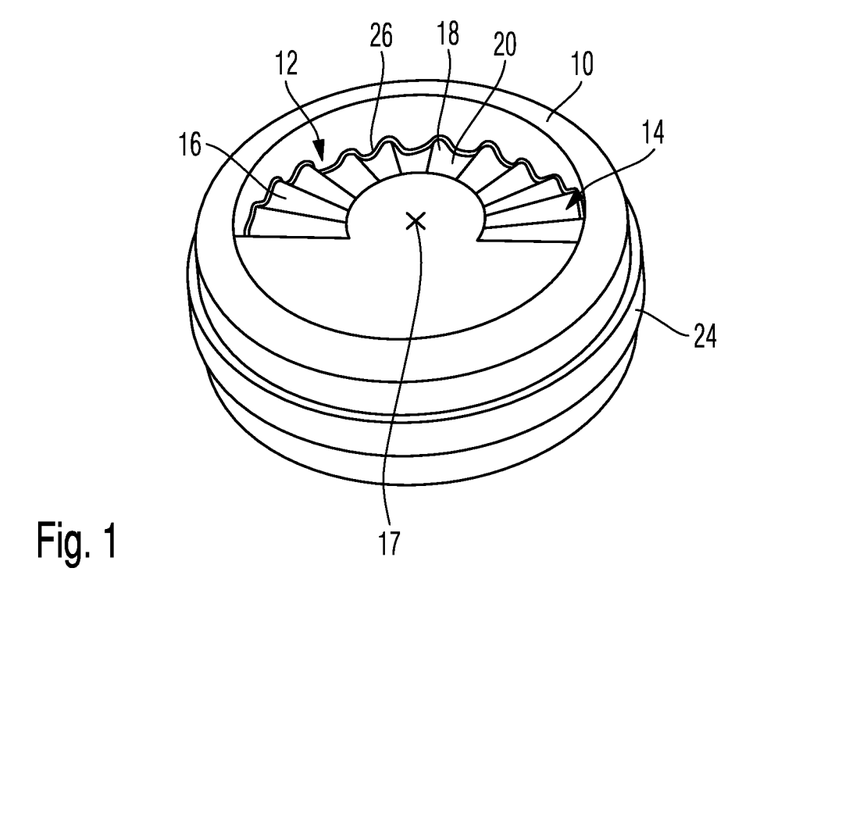
FIG. 1 shows a schematic perspective view of a blank for producing a dental prosthesis, namely a circular disc-shaped gum-colored blank.

FIG. 1 shows a gum-colored blank 10 as a primary product of an inventive dental prosthesis in an embodiment in a perspective view. The basic structure of the blank is disc-shaped and consists of gum-colored material which may also be referred to as gingival material. At its upper side—in the illustration according to FIG. 1—it comprises a recess 12 which is configured in a particular manner. Basically, the recess 12 extends in the form of a semicircle, that is to say in the shape of an arch. One of the characteristic features of the arch is the wave shape of the bottom side of the recess 12 which extends towards the arch. In the radial direction, that is to say from the center 17 of the arch towards the outside, that is to say towards the vestibular side, a radial shape is provided.

The arch 16 consists of alternating wave crests 18 and wave troughs 20. They extend isogonically such that the same wave crest exists at the same angular position of the arch 16, and the same wave trough 20 exists at another consistent angular position.

It is apparent from FIG. 1 that the wave shape 14 of the arch 16 deviates slightly from a sine shape. Indeed, the wave shape simulates the gingival margin and, in this respect, assumes some elements of a catenary and some elements of a sine shape.

The arch-shaped recess 12 is intended to receive a blank made of tooth-colored material which is shaped such that it fits the recess. Accordingly, the side of the blank made of tooth-colored material which faces the blank comprises a negative shape relative to the wave shape 14 at the bottom of the recess 12. In this respect, the shape of the tooth-colored blank exactly matches the recess 12, possibly by leaving an adhesive gap having a thickness of between 50 μm and 150 μm.

Accordingly, the tooth-colored blank may be bonded into the recess 12 of the blank 10 easily.

Alternatively, it is also possible to produce a connection between these blanks by polymerization.

By means of the joining operation, the blank 10 in turn obtains the shape of a circular disc altogether due to the filling of the recess 12, wherein in a way known per se an annular protrusion 24 is configured circumferentially and serves to be mounted in the workpiece holder of a dental milling machine.

In this connection, it is provided to mount the blank 10 at an exactly predetermined position by means of a positioning device which enables to mount the blank such that rotation is prevented. Thus, the blank which has possibly been machined partially may be removed for inspection purposes if necessary, and may then be reinserted in the correct position.

According to the invention, after the two blanks have been connected with one another intensively in the described manner or in any other suitable manner, the milling process which is predetermined by CAD/CAM is performed. The blank produced in this way makes it possible to realize any design of prostheses, that is to say prosthesis bases and teeth. The entire dental prosthesis may be produced in one go by milling, and the gingival line 26 makes possible that the gingival margin provided in this way may not be differentiated from a natural gingival margin at first glance.

Even if the recess 12 is described as a circular arc-shaped recess, it is to be understood that any other configurations of the shape are possible. As is indicated in FIG. 1 the wave shape 14 is indeed lowered slightly in the vestibular/incisal area, and raised slightly in the vestibular/molar area, in accordance with the human gingival margin.

Figure 2:
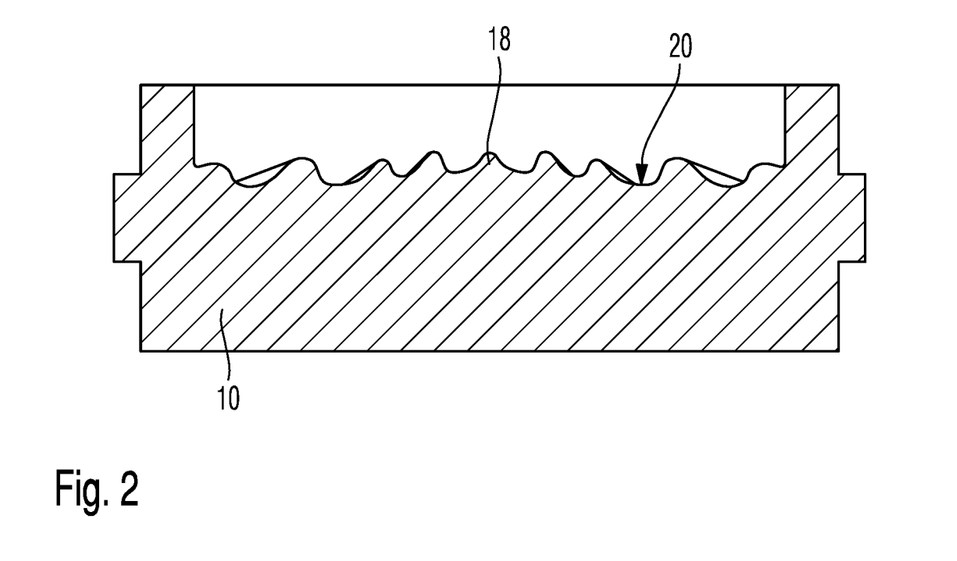
FIG. 2 shows the illustration according to FIG. 1 in a sectional view.

A possible distribution of the wave crests and wave troughs is apparent from the sectional view of the blank 10 illustrated in FIG. 2. The radial shape of the wave crests 18 or wave troughs 20, respectively, produces an asymmetric distribution of the wave crests and wave troughs, as can be seen from FIG. 2.

The arch width of the arch 16—as viewed in the radial direction—is considerably larger than the vestibular/lingual or vestibular/palatal extension of a prosthesis tooth.

In this way, it is initially possible to determine any desired radial position of the dental arch to be provided for by CAD. Thus, the size of the prosthesis, but also of the associated teeth, may be adapted to the requirements of the human jaw of the patient to a large extent. Due to the radial shape, in case of smaller arches smaller teeth are produced automatically as the distance between two crests 18 or between two troughs 20 corresponds to the grid dimension of the teeth, respectively.

According to the invention, it is particularly favorable that the inserted teeth will not be separated even after the milling process but are present in the form of a dental arch. The interdental spaces are preferably configured to be positioned deeply and the bridges of material between the individual teeth are shifted towards the lingual/palatal side. In this way, it is ensured that the optical impression of the inventive dental arch may not be differentiated virtually from a set of teeth with individual teeth.

Realizing the dental arch additionally allows for considerably increased strength.

This makes it possible to manage with teeth without tooth roots, that is to say teeth which are only held in position by means of the intensive connection with the gingival blank 10.

It is favorable to realize the recess 12, as is illustrated in FIG. 1 and FIG. 2, in order to precisely position the tooth blank relative to the gingival blank.

Figure 3:
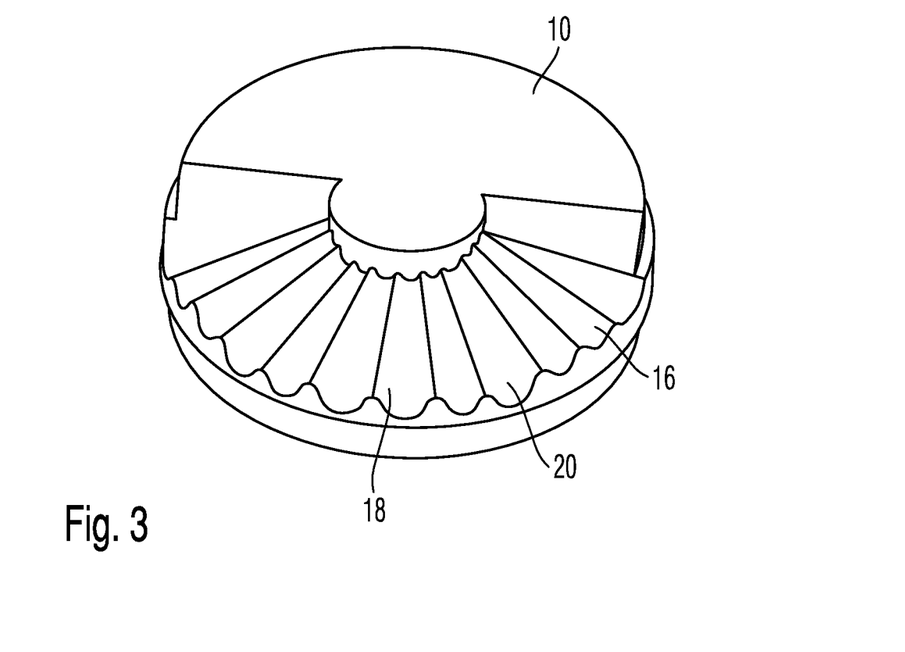
FIG. 3 shows a modified embodiment of the blank according to FIG. 1.

In a modified embodiment, however, the arch 16 extends until the outer circumference of the blank 10, as is apparent from FIG. 3. This embodiment, too, is suitable for forming a prosthesis base which fits many different sizes and shapes, wherein this embodiment also enables slightly enlarged dental arches.

FIG. 3 shows a homogeneous distribution of the wave troughs 20 and the wave crests 18. In a still further modified embodiment it is provided to realize the wave crests and troughs to be narrower and smaller in the area of the incisors, and accordingly to realize them broader and of a larger height in the area of the premolars and above all the molars. This accounts for the different tooth sizes and tooth widths along the course of a human set of teeth.

However, a human set of teeth is typically not exactly shaped like a circular arc, but recedes slightly in the incisal area, that is to say in particular in the area of the teeth I, which have an almost plane labial surface, compared to a circular arc. Then, the radial shape of the crests 18 and troughs 20 automatically leads to smaller grid dimensions thereat.

On the other hand, human upper jaw teeth II are typically slightly narrower than the upper jaw teeth I. This can also be taken into account by correspondingly adapting the width of the troughs and crests to the respective angular position, particularly in the case of upper jaw prostheses.

Figure 4:
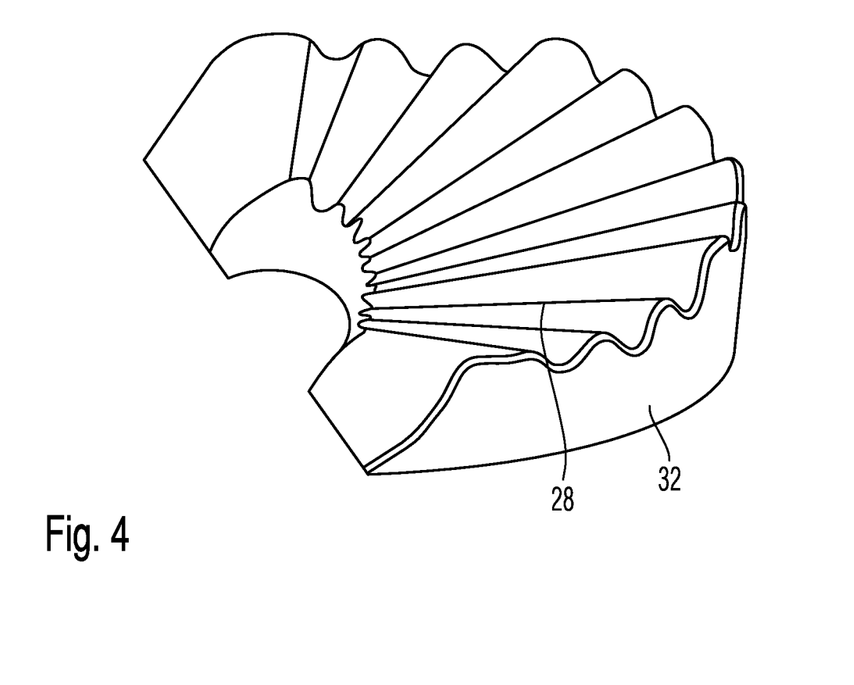
FIG. 4 shows a further modified configuration of a dental arch blank for providing an inventive dental prosthesis.

In comparison, an even further modified dental arch blank 32 is apparent from FIG. 4. The shape of the wave crests and wave troughs extending radially and apparent from the FIG. 4 fits the prosthesis base blank 10 in a manner true to shape, into the recess 12 disposed thereat.

In this embodiment the rays 28 extend towards a central point which is considerably lowered relative to the height of the gingival line. In this way, the rays 28 are caused to tilt relative to the horizontal which is favorable in particular embodiments and enables a better mounting of the dental arch in the palatal/lingual region.

Figure 5:
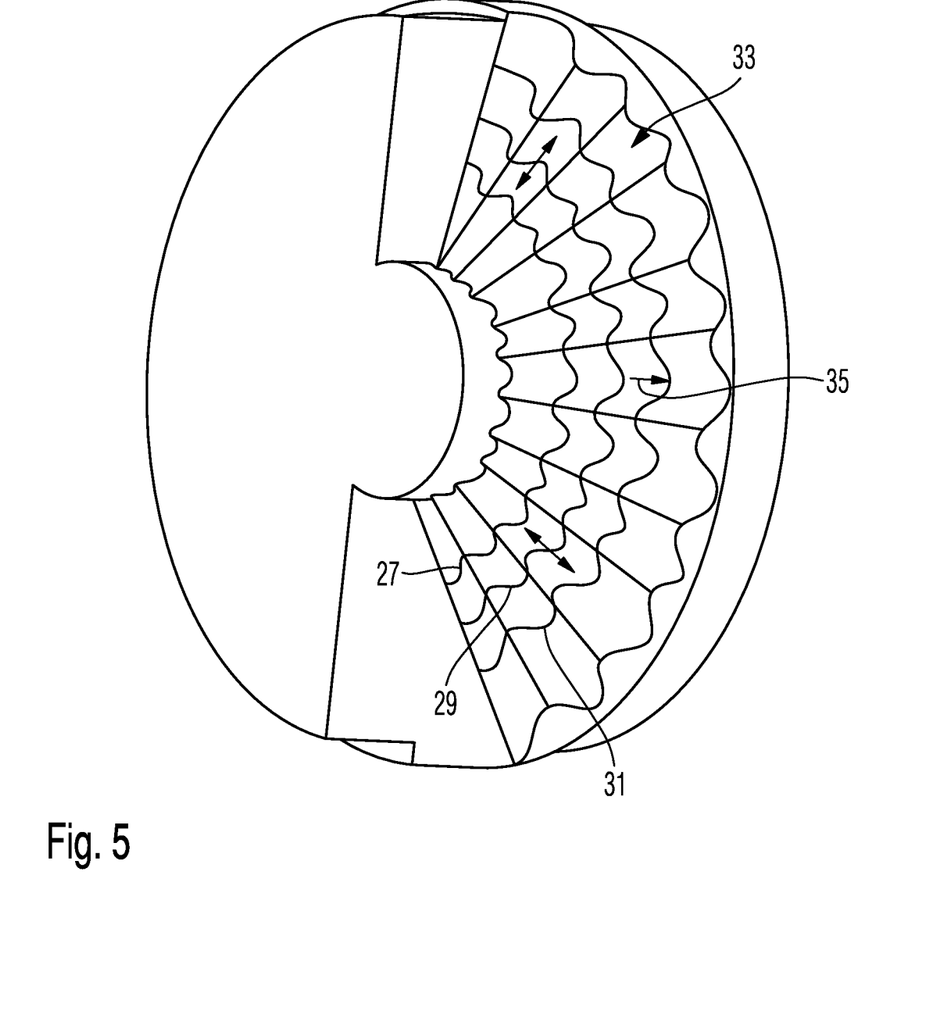
FIG. 5 shows a view of the prosthesis base blank showing indicated possible border lines of the interface to form the gingival margin.

FIG. 5 shows an accordingly exposed, partially machined prosthesis base blank 10 which illustrates the tilt of the radial line 28 described in connection with FIG. 4. Moreover, various border lines 27, 29 and 31 are indicated in FIG. 5 which exemplify the milling line of the interface 33 with respect to the dental arch blank 32 which is to be seen as the prosthesis gingival margin, in this respect.

Its position may be adjusted by the control device in a patient-specific manner wherein in case of rather triangle-shaped jaw structures the mesial region protrudes in accordance with the arrow 35, and the line structure apart from that may be adapted to the requirements to a large extent.

Figure 6:
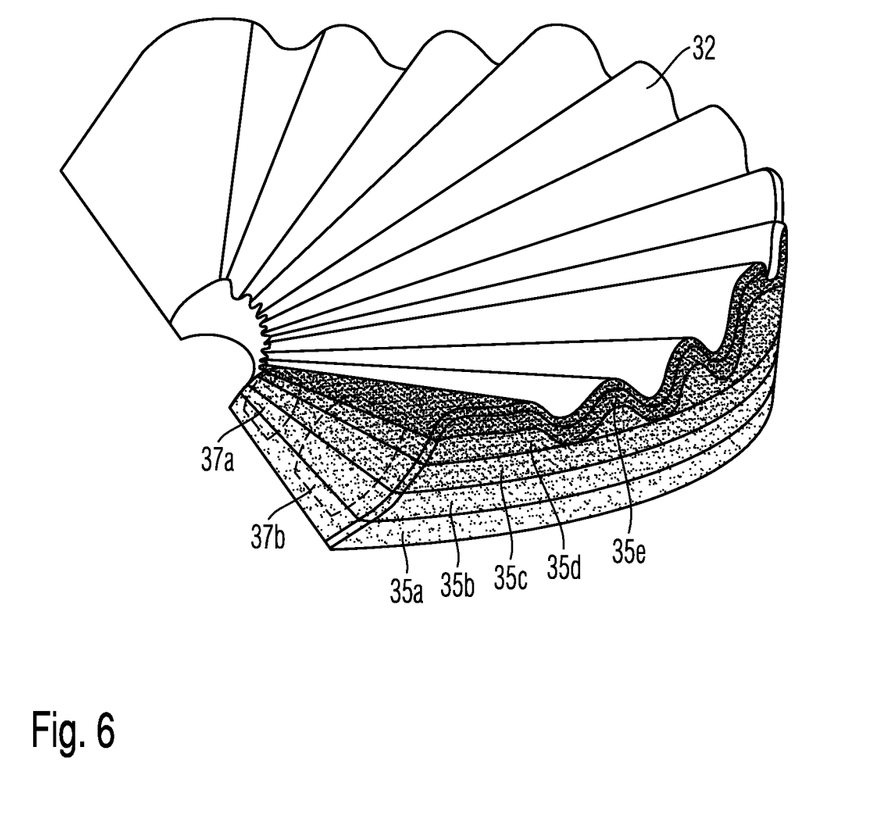
FIG. 6 shows a further modified configuration of the dental arch blank according to FIG. 4.

FIG. 6 shows how a dental arch 32 which is to be mounted in a recessed manner in a circular arc recess in the partially machined prosthesis base blank 10 may be built in layers.

It is apparent schematically that the dental arch blank 32 is built from 5 layers 35a, 35b, 35c, 35d and 35e which become increasingly dark and opaque towards the interface 33, corresponding to the dentin of a human tooth. It is to be understood that considerably more or also fewer layers may be used.

Here, the layer transition 35e-35d follows the course of the rays, wave crests and wave troughs of the interface in an extenuated manner, while this characteristic becomes more and more extenuated towards the layer 35a. Examples of tooth shapes and sizes, 37a and 37b, are shown in dashed lines.

It is to be understood that here the two blanks are preferably each produced separate from one another by milling and are then joined together and connected with one another intensively by adhesive bonding. During milling, the side flanks of the circular arc recesses to be seen thereat form stops of the inventive dental arch in the mesial/distal direction likewise. This enables a particularly good anchorage of the dental arch as is particularly important with comparatively small prostheses.

By milling off the outer side of the prosthesis base blank 10 the inventively particularly favorable gingival line between red and white material can be made visible, in turn.

Figure 7:
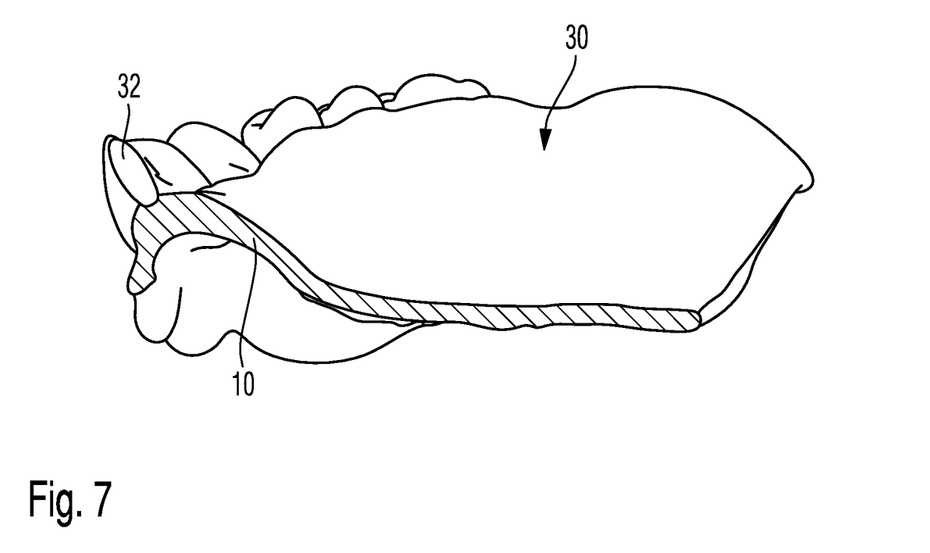
FIG. 7 shows a finished dental prosthesis in one embodiment in a sectional view.

FIG. 7 shows how a finished prosthesis 30 may be configured in cross-section.

It is apparent that the tooth-colored material 32 extends along the prosthesis base 10 produced in this way according to the gingival margin, but without perforating the gum-colored material 10, according to the natural dental arch. It is also apparent that in this preferred embodiment the material 32 is also held positively in the material 10 in the radial direction.

Figure 8:
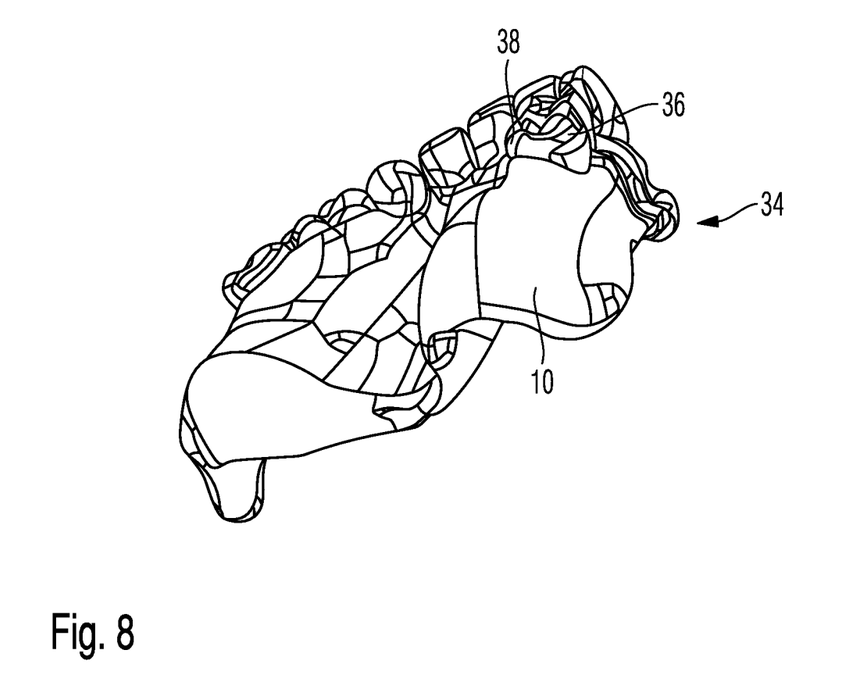
FIG. 8 shows a further embodiment of a prosthesis according to FIG. 7.

FIG. 8 shows the finished dental prosthesis 34 with the aid of a wire model. By reference to the rearmost molar 36 as part of the inventive dental arch 38 it is apparent that it is embedded intensively in gingival material or connected with it intensively, respectively.

Figure 9A:
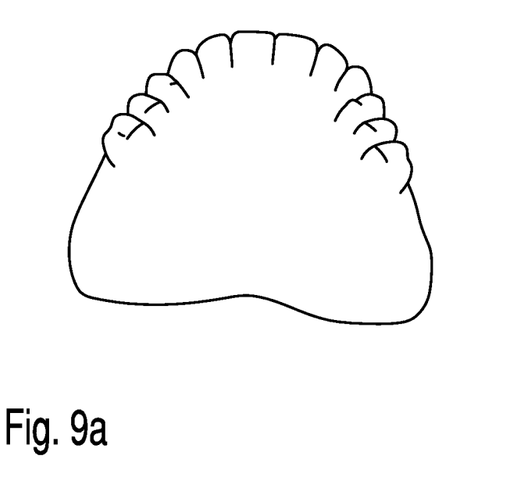
FIG. 9a show further embodiments of inventive dental prostheses in the finished state.
Figure 9B:
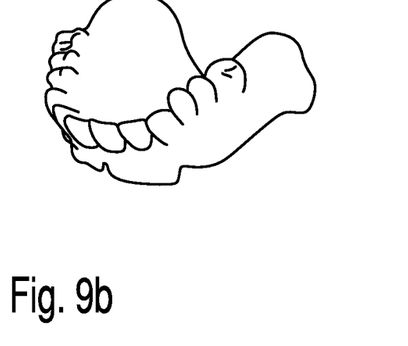
FIG. 9b show further embodiments of inventive dental prostheses in the finished state.

FIGS. 9a and 9b show prostheses produced accordingly in different directions of view in perspective.

Figure 10:
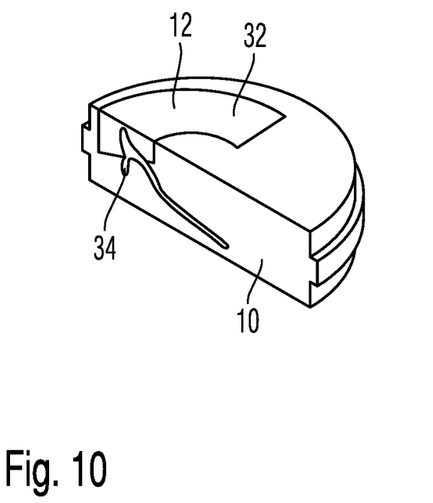
FIG. 10 show schematic illustrations of the blanks for providing an inventive prosthesis, also illustrating the tooth-colored blank.
Figure 10A:
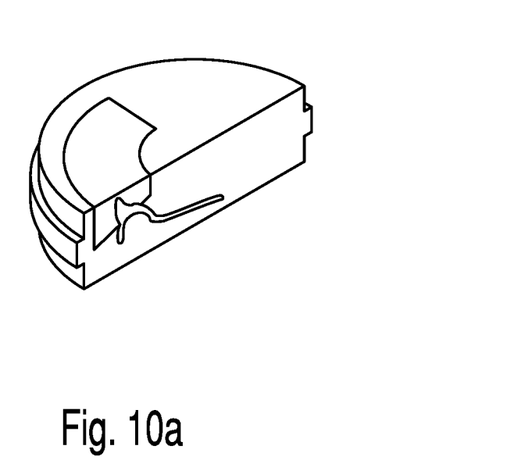
FIG. 10a show schematic illustrations of the blanks for providing an inventive prosthesis, also illustrating the tooth-colored blank.

FIG. 10 and FIG. 10a show how the arch-shaped tooth-colored material 32—still in the shape of a blank in this illustration—is inserted into the recess 12 of the blank 10 and accommodated therein. The subsequent shape of the prosthesis 34 is illustrated schematically in FIG. 10 and FIG. 10a, respectively.

Figure 11:
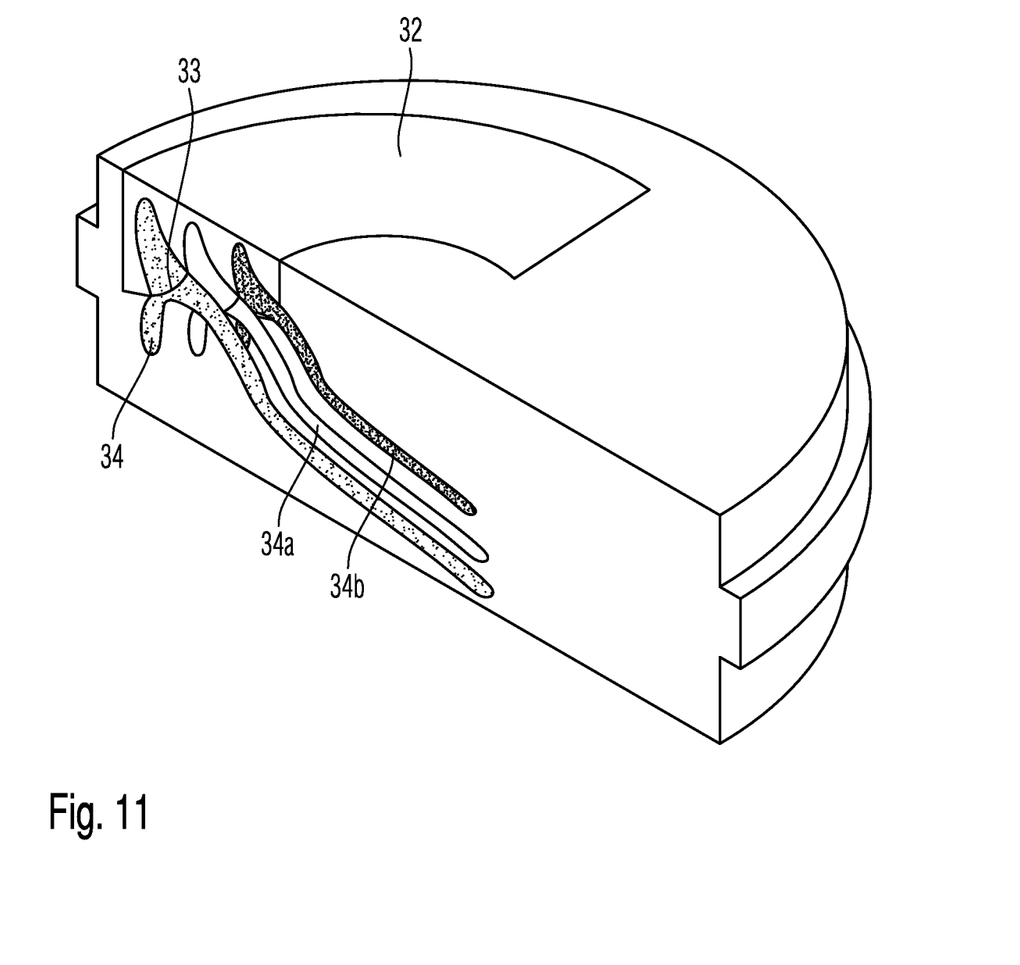
FIG. 11 shows a schematic illustration of the blank according to FIG. 10 wherein various dental arch sizes are indicated alternatively.

FIG. 11 shows a section according to FIG. 10 wherein different prostheses 34, 34a and 34b are illustrated with alternative sizes. It is apparent that the blank 10 leaves sufficient free space for the largest possible combinations of prosthesis bases and teeth both towards the occlusal/incisal side, that is to say in the region of the dental arch 32, and in the central region towards the bottom, wherein it is to be understood that the dimensions of the blank are known as boundary conditions to the control device.

The invention claimed is:

1. A method of producing a dental prosthesis comprising
providing a one-piece or multi-piece prosthesis blank having a gum-colored material and a tooth-colored material connected to each other at connecting surfaces and having an interface between the gum-colored and the tooth-colored materials, the interface, when viewed along the connecting surfaces, has an undulating shape and when viewed in a vestibular direction has a radial shape,
using a CAD/CAM device to determine an exact course of a gingival line based on patient-specific data in order to produce and finish the dental prosthesis.

2. The method of producing a dental prosthesis according to claim 1, comprising
supplying the CAD/CAM device with the patient-specific data, where anatomically relevant points are marked and serve as reference points.

3. The method of producing a dental prosthesis according to claim 2, comprising
obtaining the patient-specific data from an intraoral 3D scan or an impression.

4. The method of producing a dental prosthesis according to claim 1, comprising
using the CAD/CAM device to automatically produces a suggestion for the prosthesis.

5. The method of producing a dental prosthesis according to claim 4, comprising
using the CAD/CAM device to produce the prosthesis as a virtual prosthesis.

6. The method of producing a dental prosthesis according to claim 5, comprising
changing the virtual prosthesis by a user at the CAD/CAM device.

7. The method of producing a dental prosthesis according to claim 1, comprising using the CAD/CAM device having a design function to constructs and produce a vestibular border line of the interface based on the patient-specific data.

8. The method of producing a dental prosthesis according to claim 1,
wherein the gum-colored material (10) is removed by milling.

9. The method of producing a dental prosthesis according to claim 1,
wherein a plurality of dental arches or dental parts can be produced from one input material blank.

10. The method of producing a dental prosthesis according to claim 1,
wherein the radial shape ensures that, when the width increases as viewed from the vestibular direction, the height of the teeth and wave crests increases at the same time.

11. The method of producing a dental prosthesis according to claim 1,
wherein in smaller arches, smaller teeth are produced automatically, due to the radial shape of the dental prosthesis, as the distance between two crests or between two troughs corresponds to the grid dimension of the teeth.

12. The method of producing a dental prosthesis according to claim 1,
wherein the data is fed to a rapid prototyping device in which the shapes of the tooth arch blank and the prosthesis base blank are stored virtually.

13. The method of producing a dental prosthesis according to claim 12,
wherein the tooth arch blank and the prosthesis base blank comprise a radial/wave-shaped interface.

14. The method of producing a dental prosthesis according to claim 1, comprising
providing the one-piece or multi-piece prosthesis blank having the gum-colored material and the tooth-colored material are fabricated of a plastic material.

15. The method of producing a dental prosthesis according to claim 1, comprising
providing the one-piece or multi-piece prosthesis blank having the gum-colored material and the tooth-colored material intensively connected to one another.

* * * * *